US006232119B1

(12) United States Patent
Prasad et al.

(10) Patent No.: US 6,232,119 B1
(45) Date of Patent: May 15, 2001

(54) IMMORTALIZED HUMAN FETAL NEURONAL CELL LINE

(75) Inventors: Kedar N. Prasad; Curt R. Freed, both of Denver, CO (US)

(73) Assignee: University Technology Corporation, Boulder, CO (US)

(*) Notice: Subject to any disclaimer, the term of this patent is extended or adjusted under 35 U.S.C. 154(b) by 0 days.

(21) Appl. No.: 09/097,212

(22) Filed: Jun. 12, 1998

Related U.S. Application Data (60) Provisional application No. 60/049,758, filed on Jun. 13, 1997, and provisional application No. 60/049,801, filed on Jun. 17, 1997.

(51) Int. Cl.[7] .............................. C12N 5/08; C12N 5/00; C12N 15/63

(52) U.S. Cl. ......................... 435/368; 435/325; 435/366; 435/377; 435/455

(58) Field of Search ............................. 514/44; 435/325, 435/320.1, 69.1, 366, 368, 377, 455; 536/23.5; 424/93.2

(56) References Cited

U.S. PATENT DOCUMENTS

| | | | |
|---|---|---|---|
| 5,082,670 | 1/1992 | Gage .................................... | 424/520 |
| 5,196,315 | 3/1993 | Ronnett ................................. | 435/29 |
| 5,650,148 | * 7/1997 | Gage et al. .......................... | 424/93.2 |
| 5,690,927 | 11/1997 | Major ................................. | 424/93.21 |
| 5,753,491 | * 5/1998 | Major et al. ...................... | 435/240.2 |
| 5,753,506 | 5/1998 | Johe .................................... | 435/377 |
| 5,869,463 | * 2/1999 | Major et al. ........................ | 514/44 |
| 6,045,807 | * 4/2000 | Gage et al. ......................... | 424/368 |

OTHER PUBLICATIONS

Freed, W.J. et al. "Genetically altered and defined cell lines for transplantation in animal models of Parkinson's disease" (1990) *Progress in Brain Research* 82:11–21.

Adams, F.S. et al. "Characterization and transplantation of Two Neuronal Cell Lines with Dopaminergic Properties"(1996) *Neuro. Chem. Res.* 21:619–627.

Anton, R. et al. "Neural–Targeted Gene Therapy for Rodent and Primate Hemiparkinsonism" (1994) *Exp. Neurology* 127:207–218.

Augusti–Tocco, G et al. "Establishment of Functional Clonal Lines of Neurons from Mouse Neuroblastoma" (1969) *Proc. Natl. Acad. Sci. USA* 64:311–315.

Freed, W.J. et al. "Properties of PC12 Pheochromocytoma Cells Transplanted to the Adult Rat Brain" (1986) *Exp. Brain Res.* 63:557–566.

Kordower, J.H. et al. "Neuroblastoma cells in neural transplants: a neuroanatomical and behavioral analysis" (1987) *Brain Research* 417:85–98.

Prasad, K.N. et al. "Production of terminally differentiated neuroblastoma cells in culture" (1994) *Restor. Neurol. Neurosci.* 7:13–19.

Prasad, K.N. et al. "Establishment and Characterization of Immortalized Clonal Cell Lines from Fetal Rat Mesencephalic Tissue" (1994) *In Vitro Cell Div. Biol.* 30A:596–603.

Prasad, K.N. et al. "Basal Level of Neurotransmitter Synthesizing Enzymes and Effect of Cyclic AMP Agents on the Morphological Differentiation of Isolated Neuroblastoma Clones" (1973) *Nature New Biol.* 241:117–119.

Rosenberg, M.B. et al. "Grafting Genetically Modified Cells to the Damaged Brain: Restorative Effects of NGF Expression" (1988) *Science* 242:1575–1578.

Ryder, E.F. et al. "Establishment and Characterization of Multipotent Neural Cell Lines Using Retrovirus Vector–Mediated Oncogene Transfer" (1990) *J. Neurobiol.* 21:356–375.

Schubert, D. et al. "Clonal Cell Lines from the Rat Central Nervous System" (1974) *Nature* 249:224–227.

Tumilowicz, J.J. et al. "Definition of a Continuous Human Cell Line Derived from Neuroblastoma" (1970) *Cancer Research* 30:2110–2118.

Clarkson, E.D. et al. "Improvement of neurological deficits in 6–hydroxydopamine–lesioned rats after transplantation with allogeneic simian virus 40 large tumor antigen gene–induced immortalized dopamine cells" (1998) *Proc. Natl. Acad. Sci. USA*, 95:1265–1270.

Freed, C.R. et al. "Survival of Implanted Fetal Dopamine Cells and Neurologic Improvement 12 to 46 months after Transplantation for Parkinson's Disease" (1992) *The New England Journal of Medicine*, 327(22):1549–1555.

Freed, C.R. et al. "Transplantation of Human Fetal Dopamine Cells for Parkinson's Disease" (1990) *Arch Neurol.* 47:505–512.

Spencer, D.D. et al. "Unilateral Transplantation of Human Fetal Mesencephalic Tissue into the Caudate Nucleus of Patients with Parkinson's Disease" (1992) *The New England Journal of Medicine* 327(22):1541–1548.

Adams et al., "Characterization and Transplantation of Two Neural Cell Lines with Dopaminergic Properties." *Neurochem. Res.*, vol. 21 (5): 619–627, 1996.*

Bankiewicz et al., "Practical Aspects of the Development of ex Vivo and in Vivo Gene Therapy for Parkinson's Disease." *Exp. Neurology*, vol. 144: 147–156, 1997.*

Raymon et al., "Application of ex Vivo Gene Therapy in the Treatment of Parkinson's Disease." *Exp. Neurology*, vol. 144 : 82–91, 1997.*

(List continued on next page.)

Primary Examiner—Deborah Crouch
Assistant Examiner—Quang Nguyen
(74) *Attorney, Agent, or Firm*—Greenlee, Winner and Sullivan, P.C.

(57) ABSTRACT

An immortalized line of human fetal brain cells capable of synthesizing dopamine has been developed. No tumor formation or rejection at 30 days post-transplantation has been detected. The cells are useful for transplantation therapy of a neurological deficit characterized by dopamine deficiency in the local region of the brain.

11 Claims, 3 Drawing Sheets

OTHER PUBLICATIONS

Horellou et al., "Gene Therapy for Parkinson's Disease." Molecular Neurobiol., vol. 15: 241–256, 1997.*

Prasad et al., "MiniReview–Efficacy of Grafted Immortalized Dopamine Neurons in an Animal Model of Parkinsonism: A Review." Molecular Genetics and Metabolism, vol. 65: 1–9, 1998.*

Cattaneo et al., "A short term analysis of the behaviour of conditionally immortalized neuronal progenitors and primary neuroepithelial cells implanted into the fetal rat brain." Dev. Brain Research, vol. 83: 197–208, 1994.*

Scheffler et al., "Marrow–mindedness : a perspective on neuropoiesis." TINS, vol. 22 (8): 348–357, 1999.*

Sanberg et al., "Cellular therapeutic approaches for neurodegenerative disorders." Proceedings of the 1998 Miami Bio/Tech. Winter Symposium, Nucleic acids symposium series No. 38, pp. 139–142, Feb. 1998.*

Frederiksen et al., "Immortalization of precursor cells from the mammalian CNS." Neuron, vol. 1: 439–448, Aug. 1988.*

Clarke et al., "Human fetal dopamine neurons grafted in a rat model of Parkinson's disease: ultrastructural evidence for synapse formation using tyrosine hydroxylase immunocytochemistry." Experimental Brain Research, vol. 73: 115–126, 1988.*

* cited by examiner

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear    (ii) MOLECULE TYPE: other nucleic acid
      (A) DESCRIPTION: /desc = "oligonucleotide"

-continued

```
    (xi) SEQUENCE DESCRIPTION: SEQ ID NO:1:

GGGGAGCTGA AGGCTTATGG                                                 20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:2:

GGACACAAAG TACACAGGCT                                                 20

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:3:

TATGGCACAG AAGCACAATG TGCCCA                                          26

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide"

(iii) HYPOTHETICAL: NO (xi) SEQUENCE DESCRIPTION: SEQ ID NO:4:

AGCCAGGACA ATGCCAAGAG TGAAGA                                          26
```

IMMORTALIZED HUMAN FETAL NEURONAL CELL LINE

CROSS REFERENCE TO RELATED APPLICATIONS

This application claims priority from U.S. Provisional Application No. 60/049,758, filed Jun. 13, 1997, and from U.S. Provisional Application No. 60/049,801, filed Jun. 17, 1997.

STATEMENT RE FEDERALLY SPONSORED RESEARCH AND DEVELOPMENT

This invention was made, at least in part, with funding from the Public Health Service by Grants Numbers NS29982, NS35348 and NS18639. Accordingly, the United States Government may have certain rights in this invention.

BACKGROUND OF THE INVENTION

The replacement of dopamine (DA) by fetal mesencephalic tissues or DA-cell transplant appears to be a rational choice for the treatment of patients with advanced Parkinson's disease. Fetal mesencephalic tissues have been used extensively in animal models of Parkinson's disease See, for example, Björklund, A. et al. (1979) Brain Res. 177, 555–560; Perlow, M. F. et al. (1979) Science 204,643–647; Bakay, R. A. E. et al. (1985) Appl. Neurophysiol 48, 358–361; Freed, C. R. et al. (1988) in Pharmacology and Functional Regulation of Dopaminergic Neurons, eds. Beart, P. M., Woodruff, G. and Jackson, D. M. (Macmillan Press, London) pp. 353–360; Dunnett, S. et al. (1991) in Intracerebral Transplantation in Movement Disorders, eds. Lindvall, O., Björkland, A. and Widner, H. (Elsevier, Amsterdam) pp 27-et seq; Freed, W. J et al. (1990) Exper. Neurol. 110, 139–166; and Kordower, J. H. et al. (1994) in Neural Transplantation, CNS Neuronal Injury and Regeneration, eds. Marwah, J., Titelbaum, H. and Prasad, K. N. (CRC Press, Fla.) pp. 17–37. These studies show varying levels of improvement of neurological deficits. The use of such tissues in advanced Parkinson's disease cases also produced variable results as reported in Freed, C. R. et al. (1990) Arch. Neurol. 47, 505–512; Lindvall, 0. et al, (1992) Arch. Neurol. 31, 155–165; Madrazo, I. et al. (1990) Arch Neurol. 47, 1281–1285; and Hitchcock, E. (1992) in Recovery from Brain Damage, eds. Rose, F. D. and Johnson, D. A. (Plenum Press, N.Y.) pp. 67–78. A double-blind study with placebo control to evaluate the efficacy of fetal tissue in the treatment of neurological symptoms in patients with advanced Parkinsonism is in progress. Apart from the issue of efficacy of allogeneic fetal central nervous system (CNS) tissue in neural transplants, the use of fetal tissue is limited by ethical, legal, tissue availability, survivability and some inherent biological problems. The latter includes the presence of donor-antigen presenting cells which may induce rejection of allogeneic grafted tissues. See Freed, C. R. et al. (1990) Arch. Neurol. 47,505–512; Lindvall, O. et al. (1992) Arch. Neurol. 31, 155–165; Madrazo, I. et al. (1990) Arch. Neurol. 47, 1281–1285; Hitchcock, E. (1992) in Recovery from Brain Damage, eds. Rose, F. D. and Johnson, D. A. (Plenum Press, N.Y.) pp. 67–78. Another biological problem is heterogeneity within the population of grafted cells. In order to overcome the above difficulties, the establishment of homogeneous populations of DA—producing neurons in vitro, free of antigen presenting cells, would be invaluable. Clonal lines of transformed (tumorigenic) DA-producing neurons, such as those described in Augusti-Tocco, G et al. (1969) Proc. Natl. Acad. Sci. USA 64, 311–315; Prasad, K. N. et al. (1973) Nature New Biol. 241, 117–119; Tumilowicz, J. J. et al. (1970) Cancer Research 30, 2110–2118; Schubert, D. et al. (1974) Nature 249, 224–227; are available and have been used in neural transplant studies, but such cells produce tumors following transplantation; therefore, they may not be useful until 100% of them are terminally differentiated prior to grafting. See Freed, W. J. et al. (1986) Exp. Brain Res. 63, 557–566; and Kordower, J. H. et al. (1987) Brain Res. 417, 85-et seq.

Recently, we have reported the production of 100% terminally differentiated murine neuroblastoma ($NBP_2$) cells in culture. See Prasad, K. N. et al. (1994) Restor. Neurol. Neurosci. 7, 13–19. However, the efficacy of these cells in improving the neurological deficit in the rat model of Parkinson's disease is minimal at 30 days after transplantation. See Adams, F. S. et al. (1996) Neurochemical Research 21, 619–627. In an effort to establish another source of DA-producing cells, spontaneously or genetically engineered immortalized cells, which include TH-producing fibroblasts, dopamine—producing SV40 LTa gene induced transformed cells at permissive temperature and multipotent neural cells, are now available. See Rosenberg, M. B. et al. (1988) Science 242, 1575–1579; Anton, R. et al. (1994) Exp. Neurology 127, 207–218; and Ryder, E. F. et al. (1990) J Neurobiol. 21, 365–375. The grafting of these cells in animal models of Parkinson's disease has produced variable improvements in neurological deficits when assayed within 3 months of transplant. Recently, we have established an immortalized clone of rat DA—producing neurons ($1RB_3AN_{27}$) by transfecting fetal mesencephalon cells with the plasmid vector $pSV_3^{neo}$, which carries the large T-antigen gene from SV40 virus. See Prasad, K. N. et al. (1994) In Vitro Cell. Dev. Biol. 30A, 596–603; Adams, F. S. et al. (1996) Neuro Chem Res. 21, 619–627. When these cells or differentiated $NBP_2$ cells were grafted into the striata of 6-hydroxydopamine (6-OHDA) lesioned rats, the methamphetanine-induced turning rate was reduced in about 50% of transplanted animals at 30 days after transplantation; and there was no evidence of rejection of allogeneic cells nor tumor formation at this time. Because this observation period was considered too short for determination of the efficacy of transplanted cells in improving the neurological deficits in lesioned rats, we extended the period of observation to 6 months. In addition, we compared the relative efficacy of undifferentiated and differentiated $1RB_3AN_{27}$ cells, at improving the neurological deficits in the rat model of Parkinson's disease.

SUMMARY OF THE INVENTION

The present invention teaches improvement of neurological deficits in 6-hydroxy-dopamine lesioned rats following transplantation with allogeneic SV40 large T-antigen gene-induced immortalized dopamine cells.

The replacement of dopamine (DA) by DA neuron transplants in the treatment of advanced Parkinson's disease (PD) is a rational approach. Because of limitations associated with fetal tissue transplants, a clone ($1RB_3AN_{27}$) of SV40-large T antigen (LTa) gene-induced immortalized rat DA neurons and a line of immortalized human DA neurons were utilized in this study. These allogeneic immortalized dopamine neurons, when grafted into striata of normal rats, did not divide, did not form tumors, did not produce LTa, did not extend neurites to host neurons and were not rejected, for as long as 13 months after transplantation. Grafted cells when recultured in vitro resumed cell proliferation and LTa production, suggesting the presence of a LTa gene-inhibiting factor in the brain. The grafting of undifferentiated and differentiated 1RB$_3$AN$_{27}$ cells or differentiated murine neuroblastoma (NBP$_2$) cells into striata of 6-hydroxydopamine (6-OHDA)-lesioned rats (animal model of PD) caused a time-dependent improvement in neurological deficits (reduction in the methamphetamine-induced turning rate). At 3 months after transplantation, 100% of the animals receiving differentiated 1RB$_3$AN$_{27}$ cells, 63% of the animals receiving undifferentiated 1RB$_3$AN$_{27}$ cells, 56% of the animals receiving differentiated NBP$_2$ cells and 0% of the sham-transplanted animals showed improvements in neurological deficits. At 6 months after transplantation, there was a progressive increase in spontaneous recovery in sham-transplanted animals. These results suggest that immortalized DA neurons may hold potential for their use in transplant therapy in advanced PD patients.

It is an object of the present invention to describe a novel human cell line of immortalized neural cells capable of synthesizing dopamine.

It is a further object of the invention to provide a line of non-tumorigenic, non-immunogenic immortalized human brain cells capable of producing dopamine.

It is a further object of the invention to provide a method of making an immortalized human cell line containing cells capable of producing dopamine, where the cells are non-tumorigenic and non-immunogenic.

It is a further object of the invention to provide a method for treating a neurological deficit characterized at least in part by a localized deficiency of dopamine which method includes transplanting immortalized, non-tumorigenic, non-immunogenic human dopamine-producing neural cells at a locus near the region of dopamine deficiency.

It is a still further object of the present invention to teach an improved method of treatment by transplanting differentiated dopamine-producing cells in comparison to transplanting undifferentiated cells.

These objects and others which will become obvious to the skilled artisan are deemed to fall within the spirit and scope of the present invention and are intended be included herein.

DETAILED DESCRIPTION OF THE INVENTION

In general the terms and phrases used herein have their art-recognized meaning, which can be found by reference to standard texts, journal references and contexts known to those skilled in the art. The following definitions are provided to clarify their specific use in the context of the invention.

A cell line is a population or mixture of cells of common origin growing together after several passages in vitro. By growing together in the same medium and culture conditions, the cells of the cell line share the characteristics of generally similar growth rates, temperature, gas phase, nutritional and surface requirements. The presence of cells in the cell line expressing certain substances, for example tyrosine hydroxylase (TH) can be ascertained, provided a sufficient proportion, if not all, of cells in the line are present to produce a measurable quantity of the substance. An enriched cell line is one in which cells having a certain trait, e.g. expressing TH, are present in greater proportion after one or more subculture steps, than the original cell line.

Clonal cells are those which are descended from a single cell. As a practical matter, it is difficult to obtain pure cloned cell cultures of mammalian cells. A high degree of cell purity can be obtained by successive rounds of cell enrichment. As used herein, a cell culture in which at least 90% of the cells possess a defined set of traits is termed a cloned cell culture.

Adult nerve cells divide, if ever, only rarely in vivo and cannot be cultured in vitro. In order to establish a cell line of neural origin, the cells must be altered to allow them to replicate and be maintained indefinitely in in vitro cultures over a period of years. Cells so altered are termed "immortalized." Various methods to immortalize mammalian cells have been reported, with varying success, depending on the tissue of origin. The changes resulting in immortlization are akin to those which occur in cancer, rendering the cells capable of tumor formation. Certain viruses, notably SV-40 and polyoma virus, are known to transform infected rodent cells to render them capable of forming tumors (tumorigenic). The ability of SV-40 and polyoma virus to cause tumor transformation is conferred by a viral gene encoding a protein known as the "large T-antigen" (LTa). The genes encoding the respective LTa's of SV-40 and polyoma have been cloned and transferred into plasmid vectors such that an LTa gene can be introduced into host cells without subjecting them to virus infection. In certain instances, depending on parental host cell type, cells can be immortalized by transfection with a LTa of SV-40 or polyoma virus. In the present invention, cells of rat fetal mesencephalon were immortalized by transfection with SV-40 LTa. Surprisingly, the same method did not succeed in immortalizing human fetal mesencephalic arch cells. However, the human cells could be successfully immortalized by transfection with a gene encoding polyoma virus LTa.

A "gene encoding polyoma (or SV-40) LTa" as used herein is intended to encompass any nucleotide sequence which encodes a protein having the function of polyoma (or SV-40) LTa and which is capable of being expressed in the host cell in a quantity measurable by a known assay for LTa, such as immnunochemical staining.

"Tumorigenic" means the ability to cause tumors. It is often the case that immortalized cells are tumorigenic when transplanted into a host animal. The immortalized cells of the present invention have the unexpected property that they are not tumorigenic. In fact, they fail to divide when transplanted into host brain, although they remain viable, can be recovered from the host animal and can begin dividing again, in vitro. These properties render the cell lines and cell cultures of the invention especially useful for transplantation therapy.

"Immunogenic" means the ability of cells to elicit an immune rejection response when transplanted into a host animal. The data presented herein demonstrate that the cell lines and cloned cells of the invention are not immunogenic. Being non-immunogenic is another property of the cells lines and cloned cells of the invention that renders them especially suited for transformation therapy.

A selectable marker is a genetic determinant which makes it possible to provide culture conditions which favor the growth of cells possessing the marker, compared to cells which do not. An antibiotic resistance gene is an example of a selectable marker.

The cells of the invention are derived from fetal tissue at a stage of embryonic development before the cells have taken on morphological and functional characteristics of adult cells found in different parts of the brain. The cells are relatively undifferentiated, although they are apparently partially differentiated to the extent that some cells of the fetal mesencephalon can synthesize dopamine while others cannot. The cells of the invention can be induced to differentiate in vitro by putting dibutyryl adenosine 3',5' cyclic monophosphate (dbcAMP) in the growth medium, as measured by morphological changes in the cells so treated, in culture. Cells treated as described are termed "differentiated" herein.

The transplanting of cultured cells of the invention into the brain of an animal, including a human, is a relatively simple process. A tube of appropriate diameter is inserted to the desired region of the brain, e.g. the striata, and a suspension of cells in a physiologically acceptable carrier is allowed to flow through the tube into the brain at a controlled rate, to the desired location. A physiologically acceptable carrier can be any sort of solution having non-toxic, non-injurious components for either the cells or the tissue at the site of transplant. Typically, a physiologically acceptable carrier will include a solution of salts compatible with live cells and tissue having pH, osmolarity and chemical composition ranges known in the art, for example, Hank's buffer.

The cell lines and cloned cells of the invention are useful for treating a neurological deficit characterized by dopamine deficiency in a specific location in the brain. A deficiency of dopamine in a certain defined area of the brain, the basal ganglia or striatum, results in symptoms typical of Parkinson's Disease. By transplanting dopamine-producing cells of the invention at the locus of the deficiency, the symptoms can be alleviated.

In the treatment of a neurological deficit by transplantation, there are limitations associated with the direct transplantation of tissue, from adult or fetal sources. Availability of tissue is a source limitation. Tissue samples present a heterogeneous cell population, as well as the risk of virus contamination. Ethical and legal issues in some countries limit the use of fetal tissue. Fetal tissue can also contain antigen-producing cells that are responsible for the rejection of allogenic grafts. The availability, through the present invention, of immortalized human neurons of specific phenotype which are non-tumorigenic and non-immunogenic resolves the above limitations. Provided herein are immortalized dopamine (DA)-producing human neurons in culture, which are non-tumorigenic and non-immunogenic. The human neurons have a gene encoding polyoma virus LTa, which confers on them the ability to grow indefinitely in culture (immortalized). The cells express tyrosine hydroxylase, a neural-specific enzyme which catalyzes a rate-limiting step in the conversion of tyrosine to dopamine, and dopamine transporter protein, which binds and transports free dopamine in the synaptic spaces. Both the human cells and rat cells were non-tumorigenic, as measured by transplantation in athymic mice or into striata of normal rat brain for at least 13 months after transplantation. Transplanted cells cease to express the LTa gene after transplantation and do not reveal mitotic figures in stained sections of the grafted area. However, the cells remain viable in the transplantation host, as shown by their ability to again grow when re-cultured in vitro. The cells were shown to be non-immunogenic in the transplantation host, as demonstrated by failure to detect any inflammatory response, such as leukocyte infiltration, at the site of transplantation.

The method of making a human cell line capable of expressing tyrosine hydroxylase, and therefore of synthesizing dopamine, begins with the step of isolating a suspension of human fetal brain cells. The embryonic developmental stage of the source tissue is chosen such that the tissue should be sufficiently developed hat precursors to the dopaminergic cells of the adult can be identified and sufficiently undeveloped such that the cells are capable of dividing, do not express tissue-specific antigen or become refractory to immortalization. The tissue source exemplified herein for the human cell line was mesencephalic arch tissue from a stage 16 embryo, (0.7 cm, limb bud hand 1.1 mm wide).

The fetal cells are immortalized by transfection with a gene encoding a viral LTa. The LTa of SV-40 was effective for immortalizing rat cells; however, the human cells required polyoma LTa. Transfection is preferably accomplished by using an engineered vector, such as a plasmid, having the viral LTa gene but lacking other viral genes. Preferably the vector also carries a selectable marker gene. The plasmids pSV3$_{neo}$ and pSV5$_{neo}$, available from American Type Culture Collection, Rockville, Md., carrying the LTa gene of SV-40 a polyoma, respectively, were employed.

A general strategy for isolating a cell line of immortalized, dopamine-producing cells has been developed. Transfection can be carried out by a variety of art-recognized methods, including electroporation, liposome-mediated transformation, cationic lipid binding and the like. A variety of vectors can be employed, the primary goal being to achieve stable transformation in a portion of fetal neuron cells so that they contain a gene encoding LTa and a selectable marker gene.

The advantage of selectable marker is to select transformed cells from untransformed, dividing cells. A typical selectable marker is neomycin resistance, which renders transformed cells resistant to the neomycin family of antibiotics such as geneticin. In practice, more than 90% of cells subject to the transformation process are removed during subsequent culture in the presence of geneticin. A variety of selection systems has been reported in the literature. The choice of selection method is open to those skilled in the art, based on well-known principles and factors of practicality.

A cell line including immortalized dopamine-producing cells can be further enriched to increase the proportion of DA-producing cells. The familiar technique of single-cell cloning proved ineffective for enriching a rat cell line apparently due to strong adherence between glial cells and neural cells. In order to selectively enhance neural cell growth, a strategy was adopted for alternatively culturing the cells in different media, at least one of which selectively favor neural cell growth compared to non-neural cells. The enrichment conditions have been defined for obtaining clonal cell lines of rat dopamine producing cells—the $IRB_3AN_{27}$ line. Similar conditions can be optimized for enrichment of human DA-producing cells.

Maintenance of the immortalized cells in culture is accomplished as a matter of optimization. Different cell lines may require different media for maintenance. Rat cells were preferably maintained on RPMI medium, however, human cells were preferably maintained on MCDB-153 medium. Other maintenance media can prove optimal under other circumstances, as will be understood as a matter of optimization by those skilled in the art.

Treatment of a neurological deficit responsive to dopamine, notably Parkinson's Disease, is accomplished by transplanting cells according to the invention at or near the site of the deficit, e.g. the striatum. It is preferred to transplant differentiated cells of the invention, i.e., cells treated in vitro to induce differentiation. As noted, transplantation is simply a matter of introducing cells, suspended in a physiologically acceptable carrier at the site of the deficit, using a tube of suitable diameter. The number of cells introduced can vary, depending on the severity of the symptoms, the size of the site of deficit, and the amount of dopamine produced by the cells. Effective cell dosage for transplantation into human brain ranges from $10^5$–$10^8$ cells per dose, preferably from $10^6$–$10^7$ cells per dose.

The etiology of Parkinson's Disease is well-understood. The disease results from the loss or destruction of dopamine-producing cells in the substantia nigra. A variety of agents are known to cause loss of DA-producing cells, including chemical compounds. Therefore the symptoms of Parkinsonism can be duplicated in experimental animals, and the results of treatment are predictive of results in humans. In the studies described herein, rats treated with 6-hydroxy-dopamine (6-OHDA) develop typical muscular immobility associated with Parkinson's Disease. Treatment efficacy can be evaluated by measuring the rate of turning induced by methemphetamine, in rats having a 6-OHDA-induced lesion (neurological deficit) on one side only. The animal's muscular movements are slowed on the side affected by the lesion compared to the unaffected side. The resulting asymmetric mobility can be measured as a rate of turning after animals are given the drug methamphetamine. Effective treatment therefore reduces the turning rate compared to a baseline rate for untreated animals. The turning rate assay has been shown to be an effective predictor of efficacy in humans. Similar studies can also be carried out in primates. Primate studies are especially helpful in evaluating an effective dose range and for evaluating how long the treatment is effective.

A currently used treatment for Parkinson's Disease is the administration of L-DOPA. However, efficacy of treatment diminishes over time due to the fact that at effective dosage, patients have excessive abnormal movements alternating with freezing spells. Other treatments, such as fetal mesencephalic tissue transplantation, have been shown to be effective by replacing the lost dopamine neurons. Therefore transplantation of immortalized dopamine-producing cells can be expected to have therapeutic efficacy. The amount of dopamine produced by such cells need not be great. Indeed, overproduction of DA is undesirable as it can lead to formation of toxic metabolites. As long as the cells produce a detectable amount of DA, they can be suitable for transplantation. Other criteria, as noted, are non-tumorgenicity and non- or low-immunogenicity.

With regard to the rat cells, data described herein revealed the following features:

(a) Grafting of allogeneic $1RB_3AN_{27}$ cells into striata of normal rats revealed no evidence of cell proliferation, LTa production, tumor formation, rejection or axonal innervation at 1, 4, 8 and 13 months after transplantation;

(b) Grafted allogeneic $1RB_3AN_{27}$ cells, when recultured in vitro, resumed cell proliferation and LTa production; and (c) Grafting of differentiated $1RB_3AN_{27}$ cells was most effective in comparison to grafting of undifferentiated $1RB_3AN_{27}$ cells or differentiated murine $NBP_2$ cells in reducing amphetamine-induced turning rate in 6-OHDA lesioned rats at 3 and 6 months after grafting.

Cell Culture: The clonal line of immortalized DA-producing neurons $1RB_3AN_{27}$, which has been established in our laboratory, was used. These cells are described in Prasad, K. N. et al. (1994) *In Vitro Cell. Dev. Biol.* 30A, 596–603. Cells were grown in RPMI medium containing 10% fetal bovine serum, penicillin (100 units/ml) and streptomycin (100 μg/ml), and were maintained at 37° C. in a humidified atmosphere of 5% $CO_2$. Mycoplasma free cultures were used for all experiments. The doubling time of $1RB_3AN_{27}$ cells was about 26 hours.

A murine neuroblastoma clone ($NBP_2$), which was developed in our laboratory, was also used in this study. These $NBP_2$ cells are described in Prasad, K. N. et al. (1973) *Nature New Biol.* 241, 117–119.(14) Cells were grown in F12 medium containing 10% gammaglobulin free newborn bovine serum, penicillin (100 units/ml) and streptomycin (100 μg/ml), and were maintained at 37° C. in a humidified atmosphere of 5% $CO_2$. The doubling time of $NBP_2$ cells was about 18 hours.

Differentiating Agents: $1RB_3AN_{27}$ cells ($0.5 \times 10^6$) were plated on tissue culture dishes (100 mm) which were pre-coated with specialized substrate for 4 hrs. Specialized substrate is described in Lechner, J. G. et al. (1985) *J. Tissue Cult. Methods* 9, 43–48. Dibutyryl adenosine 3',5'-cyclic monophosphate (dbcAMP) at 2.0 mM induces morphological and biochemical differentiation in some cells as reported in Adams, F. S. et al. (1996) *Neurochemical Research* 21, 619–627. However the addition of dehydroepiandrosterone (DHEA) at 60 μg/ml were observed to enhance the level of morphological differentiation in these cells 3 days after plating. Therefore these agents were used in combination to induce optimal differentiation in $1RB_3AN_{27}$ cells. Murine neuroblastoma ($NBP_2$) cells ($0.5 \times 10^6$) were plated on regular tissue culture dishes (100 mm). 4-(3-butoxy-4-methoxy-benzyl)imidazolidin-2-one (R020-1724, 200 μg/ml), an inhibitor of cyclic nucleotide phosphodiesterase, plus a polar carotenoid, originally referred to as β-carotene (20 μg/ml), are known to induce terminal differentiation in $NBP_2$ cells; therefore, they were used in this study. See Prasad, K. N. et al. (1994) *Restor. Neurol. Neurosci* 7, 13–19. Differentiating agents were added 24 hr after plating, and growth medium and agents were changed at two days after treatment. Various biological assays including transplantation were performed at 3 days after treatment when differentiated functions were maximally expressed.

Assay of Tyrosine Hydroxylase and Dopamine Transporter Protein mRNA: $1RB_3AN_{27}$ cells ($0.5 \times 10^6$) were collected in a microcentrifuge tube. The cells were centrifuged and the supernatant was removed. An Oligotex™

Direct mRNA Isolation kit (Qiagen, Chatsworth, Calif.) was used to isolate total RNA from the cells. The RNA was quantified using a spectrophotometer to ensure that equal amounts of RNA were loaded into each reverse transcriptase polymerase chain reaction (RT-PCR) mixture. The isolated RNA was then stored at −20° C. until it was needed.

The forward primer for tyrosine hydroxylase (TH) was GGGGAGCTGAAGGCTTATGG (1161–1268) (SEQ ID NO:1) with the reverse for TH being GGACACAAAGTA-CACAGGCT (1316-1297)(SEQ ID NO:2). The forward primer for the dopamine transporter protein (DAT) was TATGGCACAGAAGCACAAT-GTGCCCA (1169–1194) (SEQ ID NO:3) with the reverse for DAT being AGCCAGGACAATG-CCAAGAGTGAAGA (1424-1399) (SEQ ID NO:4). The TH primers have previously been described in Melia, K. R. et al. (1994) *Exper. Neurol.* 130, 394–406. The reactions were carried out in a Perkin-Elmer GeneAmp PCR System 9600. The reverse transcriptase reaction synthesized cDNA from 1 $\mu$g total RNA using 2.5 $\mu$M of random hexomers, 50 U of MuL V reverse transcriptase, 20 U of RNAase inhibitor, 1 mM each of dGTP, dATP, dTTP, and dCTP, 5 mM $MgCl_2$, and 1X PCR Buffer II in a total volume of 20 $\mu$l (All reagents were from Perkin-Elmer). The mixture was incubated at room temperature for 10 min. It was then placed in the thernocycler which was set at 42° C. for 15 min., 99° C. for 5 min., and 5° C. for 5 min. After the RT reaction, the mixture was removed from the thermocycler, and 4 $\mu$l of 25 mM $MgCl_2$, 8 $\mu$l 10×PCR Buffer II, 65.5 $\mu$l of $H_2O$, 0.5 $\mu$l of 5 U/$\mu$l AmpliTaq polymerase, and 1 $\mu$l each 0.4 mM of the forward and reverse primers were added for a total volume of 100 $\mu$l. A trace amount of [$\alpha$-$^{32}$P]dCTP (1.5 $\mu$Ci) was added to the reaction. The mixture was then returned to the thermocycler. After 2 min. of denaturing at 96° C., the mixture was subjected to 30 to 35 cycles with the following settings: 96° C. for 40 sec., 58° C. for 40 sec, and 72° C. for 60 sec. Once the cycles were completed, the mixture was held at 4° C. The annealing temperature was modified for the dopamine transporter fragments from 58° C. to 62° C. All samples that were not immediately used were stored at −20° C. One tenth of each PCR product was subjected to electrophoresis using a 2% agarose gel and the dried gel was exposed to X-ray film (Amersham Life Sciences, Arlington Heights, Ill.) overnight.

Viability of Grafted Cells: The viability of grafted cells was determined by histologic sections, and by their ability to grow in vitro. The procedures for growing grafted cells in vitro were described in Adams, F. S. et al. (1996) *Neurochemical Research* 21, 619–627.

Evidence of Formation of Neurites by Grafted Cells: This was primarily determined by Bodian staining. The Bodian stain was done in order to visualize nerve fibers and nerve endings. Briefly this involves deparaffinizing the slides; soaking at 37° C. in 1% Protargol (Roboz Surgical Instruments Company, Washington D.C.) solution for 72 hours, rinsing in water, soaking in reducing solution (hydroquinone 10 g/L and formalin 2%), rinsing in water, toneing in 1% gold chloride, rinsing in water, developing in 2% oxalic acid solution, rinsing in water, treating with 5% sodium thiosulfate, rinsing with water and counterstaining with aniline blue (aniline blue 0.33 g/L, oxalic acid 6.6 g/L and phosphomolybdic acid 6.6 g/L).

Tumorigenicity and Immunogenicity of Grafted Cells: In order to determine the possibility of tumor formation in non-lesioned rats receiving transplants of undifferentiated $1RB_3AN_{27}$ cells, gross and histological examinations were performed. Rats which had received two $1RB_3AN_{27}$ transplant tracks were sacrificed at 1, 4, 8 and 13 months post-transplantation, perfused with 4% paraformaldehyde, brains removed, embedded in paraffin and then cross sectioned at 10 microns. Paraffin sections of grafted brain were stained with the Harris' hematoxylin/eosin (H&E) procedure. Briefly, this involves deparaffinizing the sections, staining with Harris' Hematoxylin (5 g/L hematoxylin, 5% ethanol, 100 g/L ammonium alum, 2.5 g/L mercuric oxide), washing with $H_2O$, soaking in ethanol, washing in water, blueing with Scott's blueing agent (Sigma), washing with water then ethanol, counterstaining with eosin-phloxine solution (eosin Y 1 g/L, phloxine 0.01 g/L, 75% ethanol, 0.4% glacial acetic acid), dehydrating by ethanol and xylene and mounting with resinous medium. The presence of inflammatory cells at the site of transplantation was considered as evidence of rejection.

Unilateral 6-OHDA Lesion: Male Sprague Dawly rats (250–350 grams, Sasco) were handled and housed in accordance with University guidelines for animal care. They were anesthetized with equithesin (3.0–4.0 ml/kg supplemented as necessary) and fixed in a stereotaxic fame. A 28 gauge cannula was lowered to the medial forebrain bundle at two sets of coordinates (from bregma: L 1.5 mm; P −4.3 mm; V 7.5 mm and L 2.0 mm; P −2.3 mm; V 7.8 mm; according to Paxinos & Watson (27)). Five $\mu$L of 6-OHDA Br (2 mg/ml in saline containing 0.1% ascorbic acid) was infused at 1 $\mu$L/min. Afterwards the cannula was left in place for two minutes prior to slow withdrawal.

Transplantation: Differentiated and undifferentiated $1RB_3AN_{27}$ cells and differentiated $NBP_2$ were suspended in RPMI at a concentration of 50,000 cells/$\mu$L, and kept on ice until implantation, which was completed within 5 hours. Animals were anesthetized with equithesin (4.0 ml/kg supplement as necessary), and fixed in a stereotaxic frame that was equipped with a motorized arm (Narishiga, Tokyo). A hole was drilled through the skull (coordinates from bregma: L 2.5 mm; P 0.0 mm) and a 20 gauge stainless-steel guide cannula was lowered 3.5 mm below the dura. The infusion cannula (26 gauge extended 4 mm beyond the end of the guide and was attached to a 25 $\mu$L gas-tight syringe (Hamilton) with plastic tubing. Prior to insertion, 4 $\mu$L of cell suspension (200,000 cells) were loaded into the infusion cannula and the syringe placed in a syringe pump. The infusion was made at 1.0 $\mu$L/min while the cannula was withdrawn at 1.0 mm/min. After four minutes, the injection was stopped and the cannula allowed to remain in place for two minutes before withdrawal. Sham-transplanted control animals underwent the same procedure except that they received only RPMI medium.

Neurological Deficits as Measured by Methamphetamine-Induced Turning Rate: Turning rate in response to methamphetamine HCl (5.0 mg/kg i.p. weight of the salt) was quantified in a flat bottomed rotometer to assess the efficacy of the lesion produced by 6-OHDA. Briefly, the rotometer consisted of a plexiglass cylinder, 20 cm in diameter. The rat was tethered to a counter with a rubber band that was fastened around its chest. Full turns, ipsis- and contralateral to the side of lesion were counted in ten minute blocks for 120 minutes. Rats which showed a rate of contraversive turning $\geq 3.0$ rpm during the period 30–120 minutes after injection of methamphetamine were used for transplant studies. Previous studies have shown that this rate of tuning indicates a neurological deficit where a unilateral DA depletion of more than 95% has occurred. See Richards, J. B. et al. (1990) *Pharmacol. Biochem. Behav.* 36, 217–223.

Apomorphine was used to evaluate the level of postsynaptic dopamine receptors in 6-OHDA lesioned rats. This is in contrast to methamphetamine which measures evocable dopamine. The rate of turning caused by apomorphine (0.05 mg/kg, s.c.) was measured for 30 minutes after injection in rats prior to transplant and at 1–6 months post-transplant. However, apomorphine induced turning rate was not used as criteria for rats receiving transplants.

Statistical Analysis: A randomized analysis appropriate for repeated measures data using a Petrondas-Gabriel-type multiple comparisons procedure was used. See Zerbe, Gary O. (1979). *Journal of the American Statistical Association*, 74, 215–221 and Zerbe, Gary O. et al. (1986) *Biometrics*, 42: 795–804. The method involves linearly interpolating between the means of the observed rpm measurements for each group and making comparisons of these interpolated curves for various time intervals.

Induction of Morphological Differentiation in $1RB_3AN_{27}$ and $NBP_2$ cells: Dibutyryl cAMP treatment of cells plated on precoated dishes was more effective in inducing morphological differentiation than those plated on regular dishes. The dibutyryl cAMP concentration of 2 mM was toxic to cells plated on regular plastic dishes (data not shown). However, it induced morphological differentiation in cells plated on precoated dishes as evidenced by the formation of neurites, but the level of morphological differentiation varied from one area of the dish to another. One area showed a high level of differentiation, whereas another area revealed a lower level of differentiation. The addition of DHEA enhanced the dibutyl cAMP-induced level of morphological differentiation, whereas DHEA by itself was ineffective (data not shown). The extent of enhancement varied from one area of the dish to another, showing areas with the highest and areas with the lowest degrees of differentiation. It should be noted that most of the cells which were treated with dbcAMP plus DHEA had become larger and rounder. The solvent treatment did not alter the morphology or the growth of cells in comparison to untreated controls.

The level of differentiation in $NBP_2$ cells treated with RO20H-1724 plus polar caroteniod was similar to that reported in Prasad, K. N. et al. (1994) *Restor. Neurol. Neurosci.* 7, 13–19.

Level of TH and DAT mRNAs: THmRNA was not detected in undifferentiated $1RB_3AN_{27}$ cells using RT-PCR. TH activity has been demonstrated by biochemical assay in these cells, as reported in Adams, F. S. et al. (1996) supra. However, DAT mRNA was readily detectable in undifferentiated $1RB_3AN_{27}$ cells using RT-PCR. Differentiation caused the appearance of TH mRNA in $1RB_3AN_{27}$ cells and an increase of DAT mRNA in $1RB_3AN_{27}$ cells.

Viability, Immunogencity and Innervation of Grafted cells: The viability of grafted undifferentiated and differentiated $1RB_3AN_{27}$ cells at 8 months posttransplant was good as evidence by histological sections, as well as by their capacity to grow in culture. There also was no evidence of leukocytic infiltration of the grafted areas. However, there was no evidence of axonal innervation by DA-cells because the growth of nerve fibers occurred only along the transplant track as seen by Bodian stain. The viability of differentiated $NBP_2$ cells was poor, as shown by the fact that there were only a few cells visible in H & E staining (data not shown).

Tumorigencity of Grafted Cells: There was no evidence of cell proliferation or tumor formation in 6-OHDA lesioned animals receiving undifferentiated or differentiated $1RB_3AN_{27}$ cells, or differentiated $NBP_2$ cells at 6 months posttransplant (not shown). There also was no evidence of tumor formation in naive animals at 8 months posttransplant and at 13 months posttransplant.

Efficacy of Grafted Cells in Reducing Methamphetamine-Induced Turning Rate in 6-OHDA Lesioned Rats: Transplantation of differentiated $1RB_3AN_{27}$ cells into striata of 6-OHDA lesioned rats produced a reduction in methamphetamine induced turning rate among 100% of transplanted animals at 3 months after grafting when none of the sham-transplanted animals showed a significant change. Grafting of undifferentiated $1RB_3AN_{27}$ cells and differentiated $NBP_2$ improved the neurological deficit in 63% and 56% of 6-OHDA lesioned rats, respectively. Animals receiving differentiated $1RB_3AN_{27}$ cells continued to show improvement in neurological deficits in 100% of transplanted animals, at 4, 5 and 6 months after grafting. However, in sham-transplanted groups, a progressive spontaneous recovery was observed at 6 months after grafting.

Figure 1:
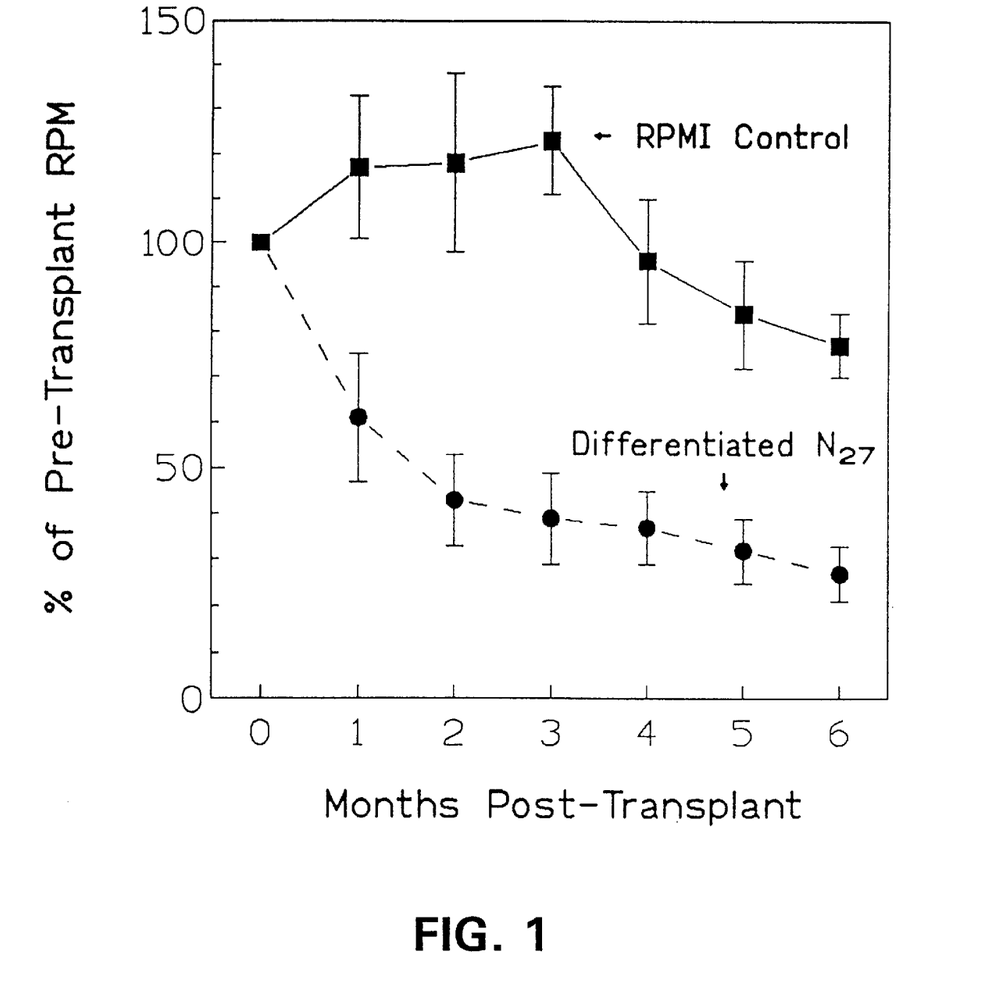
FIG. 1. Reduction of neurological deficit in animals receiving differentiated 1RB$_3$AN$_{27}$ cells. Methamphetamine-induced turning as measured in 6-OHDA lesioned animals as a function of time after grafting of 200,000 differentiated 1RB$_3$AN$_{27}$ cells into the striatum. The RPM value of treated animals at each time period was expressed as % of pretransplant RPM value. The value at each point represents an average of 8–10 samples ± SEM. RPMI Control vs differentiated 1RB$_3$AN$_{27}$ cells, $p<0.05$.
Figure 2:
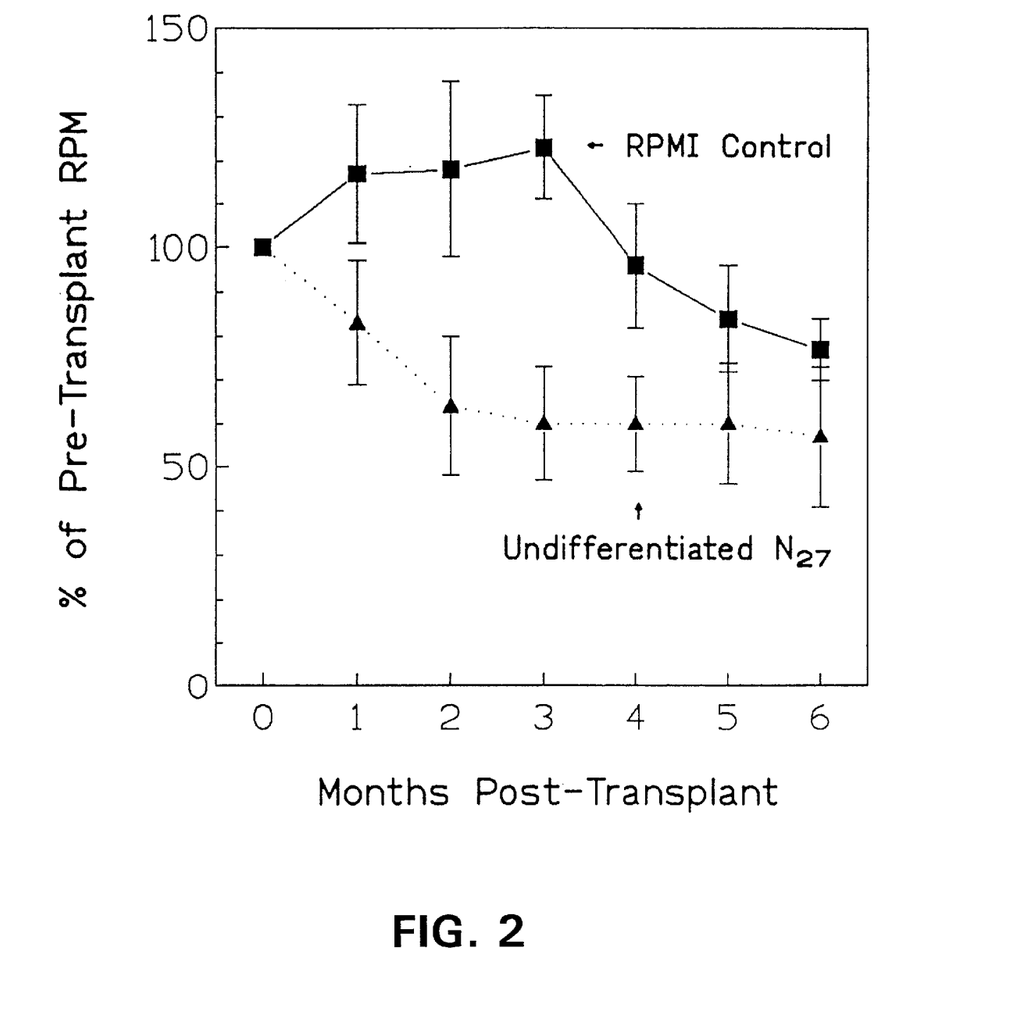
FIG. 2. Reduction of neurological deficit in animals receiving undifferentiated 1RB$_3$AN$_{27}$ cells. Methamphetamine-induced tuning as measured in 6-OHDA lesioned animals as a function of time after grafting of 200,000 undifferentiated 1RB$_3$AN$_{27}$ cells into the striatum. The RPM value of treated animals at each time period was expressed as % of pretransplant RPM value. The value at each point represents as average of 8–10 samples ± SEM. RPMI Control vs undifferentiated 1RB$_3$AN$_{27}$ cells, $p<0.05$.
Figure 3:
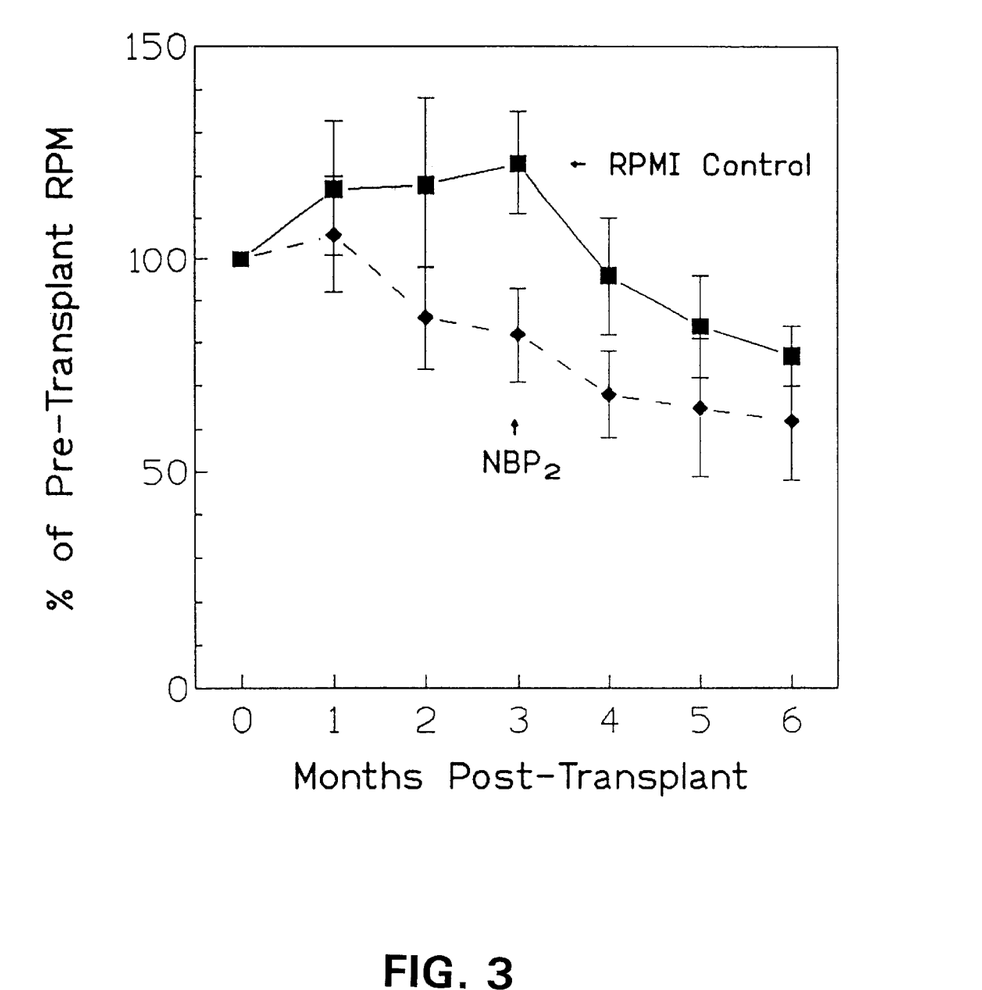
FIG. 3. Reduction of neurological deficit in animals receiving differentiated NBP$_2$ cells. Methamphetamine-induced turning as measured in 6-OHDA lesioned animals as a function of time after grafting of 200,000 differentiated NBP$_2$ cells into the striatum. The RPM value of treated animals at each time period was expressed as % of pretransplant RPM value. The value at each point represents as average of 8–10 samples±SEM. RPMI Control vs NBP$_2$ cells, $p<0.05$.

At 3 months after transplantation, the extent of reduction of methamphetamine-induced turning rate among the 6-OHDA lesioned rats, which showed improvement in neurological deficits, was similar in animals receiving differentiated (FIG. 1) or undifferentiated $1RB_3AN_{27}$ cells (FIG. 2). However, the extent of reduction of turning rate was lower in animals receiving grafts of differentiated $NBP_2$ cells (FIG. 3). The sham-transplanted animals exhibited increased turning during the first 3 months posttransplant. At 6 months after transplantation, the extent of reduction in drug-induced turning rate was most pronounced in 6-OHDA lesioned animals receiving grafts of differentiated $1RB_3AN_{27}$ cells. The grafting of undifferentiated $1RB_3AN_{27}$ cells produced greater improvement in neurological deficits than in differentiated $NBP_2$ cells or sham transplanted animals.

The apomorphine-induced tuning rate was not altered by grafted differentiated $1RB_3AN_{27}$ cells, undifferentiated $1RB_3AN_{27}$ cells or differentiated $NBP_2$ cells in 6-OHDA lesioned rats (data not shown).

Preparation of human DA-producing cell line: A single cell suspension in Hank's solution of human fetal brain (0.7 cm, stage 16, limb bud hand 1.1 mm wide) mesoncephalic arch was provided by Anatomic Gift Foundation, 13942 Baltimore Ave., Laurel, Md. 20707. Transfection with plasmid vectors $pSV3_{neo}$ or $pSV5_{neo}$ was carried out by electroporation as described for rat cells. After transfection, cells were plated in uncoated dishes containing MCDB153 medium with 10% fetal bovine serum, penicillin (100 units/ml) and streptomycin (100 µg/ml). Only cells transected by $pSV5_{neo}$ (polyoma virus LTa gene) were immortalized. At 17 days post-transfection, geneticin (200 µg/ml) was added to the culture (designated HC4M5P1) for 10 days. During this period, there was substantial cell death (mostly non-transformed cells). Survivors were allowed to grow for many passages, with samples stored frozen from passages P3–P11. For optimal growth the addition of estrogen (1 µM, insulin (10 µg/ml) and basic fibroblast growth factor (15 ng/ml) was required.

Immortalized human cells were tested by transplantation into the striata of naive rats. No tumor formation or evidence of rejection was detected 30 days post transplantation, using tests previously described for rat cells.

This study demonstrates that grafting of LTa gene-induced immortalized DA-producing neurons into striatum improves the neurological deficits in the rat model of Parkinsonism. The grafting of differentiated $1RB_3AN_{27}$ cells was more effective than the grafting of undifferentiated $1RB_3AN_{27}$ or differentiated $NBP_2$ cells in improving neurological deficits in 6-OHDA lesioned rats at 3 months and 6 months after transplantation. This may be due to the fact that differentiated $1RB_3AN_{27}$ cells exhibit increased levels of TH and DAT. The efficacy of undifferentiated $1RB_3AN_{27}$ and differentiated $NBP_2$ cells on the above criteria was similar. Previous studies have shown that the transplantation of a embryonic day 15 mesencephalon (~250,000 total cells) into 6-OHDA lesioned rats causes improvements in neurological deficits in >80% of the animals at 6 weeks posttransplant. See Brundin, P. et al. (1988) *Developmental Brain Research* 39 233–243. This value is comparable to that obtained after grafting of 200,000 differentiated $1RB_3AN_{27}$ cells. Nevertheless, the extent of improvement in neurological deficits as measured by the reduction in methamphetamine-induced turning rate was much better in animals receiving tissue transplants than those receiving differentiated $1RB_3AN_{27}$ cell transplants. It is not known whether the grafting of increased number of differentiated or undifferentiated $1RB_3AN_{27}$ cells would proportionally increase the extent of improvement in neurological deficits in 6-OHDA lesioned rats. Most of the previous studies utilizing tissues or established cell lines have limited their observation period up to 3 months after transplantation. See Björklund, A. et al. (1979) *Brain Res.* 177, 555–560; Perlow, M. F. et al. (1979) *Science* 204, 643–647; Bakay, R. A. E. et al. (1985) *Appl. Neurophysiol* 48, 358–361; Freed, C. R. et al. (1988) in *Pharmacology and Functional Regulation of Dopaminergic Neurons,* eds. Beart, P. M., Woodruff, G. and Jackson, D. M. (Macmillan Press, London) pp. 353–360; Dunnett, S. et al. (1991) in *Intracerebral Transplantation in Movement Disorders,* eds. Lindvall, O., Björkland, A. and Widner, H. (Elsevier, Amsterdam) pp 27-et seq.; Freed, W. J. et al. (1990) *Exper. Neurol.* 110, 139–166; Kordower, J. H. et al. (1994) in *Neural Transplantation, CNS Neuronal Injury and Regeneration,* eds. Marwah, J., Titelbaum, H. and Prasad, K. N. (CRC Press, Fla.) pp. 17 14 37; Freed, W. J. et al. (1986) *Exp. Brain Res.* 63, 557–566; and Kordower, J. H. et al. (1987) *Brain Res.* 417, 85-et seq. Our present study shows that the efficacy of grafted $1RB_3AN_{27}$ cells in improving neurological deficits in 6-OHDA lesioned rats persists at least 6 months after transplantation. It should be noted that at 6 months after transplantation, there was a tendency of spontaneous recovery among sham-transplanted groups.

The grafted $1RB_3AN_{27}$ cells were viable for the entire period of observation, since they can be re-cultured in vitro and their presence can be demonstrated along the transplantation track in H & E sections. In contrast, only a few differentiated murine $NBP_2$ cells were detectable in H & E sections.

Our present study shows that the rate of turning induced by apomorphine (post-synaptic DA stimulation) was not reduced in 6-OHDA lesioned rats receiving cell transplants. This observation is consistent with the histological observation using Bodian staining that the grafted undifferentiated or differentiated $1RB_3AN_{27}$ cells do not form synapses or neuronal connections. It appears that dopamine released into striatum by diffusion from $1RB_3AN_{27}$ cells is sufficient to improve the neurological deficits in 6-OHDA lesioned rats. This is analogous to improvement seen in patients with Parkinsonism after Levodopa therapy which provides needed dopamine to the striatum.

One of the major concerns in the transplantation community is that the use of oncogene-induced immortalized cells may not be practical. This is because of the potential danger of malignant transformation of either grafted cells themselves or host cells which may incorporate the oncogene following lysis of grafted cells. Our present observation shows that grafted SV40 LTa gene-induced immortalized DA-cells do not form tumors as late as 18 months after transplantation. This observation suggests that such immortalized cells may be grafted into brain without significant danger of tumor formation. This is due to the fact that brain contains LTa gene-inhibiting factors which block the production of LTa and thereby cell proliferation in grafted cells in vivo. See La Rosa, F. G. et al. (1997) *Cancer Letters* 113, 55–60.

Another major concern in the transplantation community is the issue of rejection of allogeneic cells or tissue. Allogeneic tissues are prone to rejection because it is difficult to remove all donor-antigen presenting cells primarily responsible for the induction of allo-immunization. See La Rosa, F. G. etal. (1990) *Transplantation* 49, 605–609. Although viral oncogene-induced immortalized cells are free from donor-antigen presenting cells, they may provoke a host immunological response for rejection due to presence of viral proteins. However, our present observation shows no evidence of any inflammatory response illicited by grafted differentiated or undifferentiated $1RB_3AN_{27}$ cells. These results suggest that SV40 large T-antigen gene-induced immortalized DA neurons may serve as an unlimited source of cells for transplant therapy and should be investigated for their potential use in advanced cases of parkinson's disease. Such cells are neither tumorigenic nor immunogenic by the tests described herein.

We claim:

1. A cell line of human fetal neuronal cells comprising a gene encoding polyoma virus large T antigen operably linked to a promoter and expressing tyrosine hydroxylase, wherein said cells are immortalized.

2. The cell line of claim 1 wherein said cells are non-tumorigenic when transplanted into the brain of a mammal and can grow and replicate in in vitro culture.

3. The cell line of claim 1 wherein the cells are non-immunogenic after transplantation into the brain of a mammal.

4. A cell line according to claim 1 wherein at least 50% of the cells synthesize dopamine.

5. A cell line according to claim 1 wherein at least 90% of the cells synthesize dopamine.

6. Method of making a cell line expressing tyrosine hydroxylase (TH) comprising:

isolating a suspension of human fetal neuronal cells, transfecting said cells with a gene encoding polyoma large T antigen operably linked to a promoter and a selectable marker, thereby producing a culture containing transfected cells, and enriching said culture for transfected human fetal neuronal cells expressing TH, wherein the step of enriching the culture comprises growing subclones of cells expressing TH in alternating media conditions, at least one set of conditions being differentially favorable for growth of neuronal cells compared to glial cells, and whereby an immortalized cell line expressing TH is obtained.

7. The method of claim 6 further comprising the step of growing the cells in a medium comprising estrogen, insulin and basic fibroblast growth factor.

8. A cell culture comprising immortalized human fetal neuronal cells comprising a gene encoding polyoma virus large T antigen operably linked to a promoter and expressing TH, in a medium capable of sustaining growth and replication of the cells.

9. The cell culture of claim 8 wherein the cells are non-tumorigenic when transplanted into the brain of a mammal and can grow and replicate in in vitro culture.

10. The cell culture of claim 8 wherein the cells are non-immunogenic after transplantation into the brain of a mammal.

11. The cell culture of claim 8, wherein the medium comprises estrogen, insulin and basic fibroblast growth factor.

* * * * *